(12) United States Patent
Shevitz

(10) Patent No.: US 9,050,547 B2
(45) Date of Patent: Jun. 9, 2015

(54) SCREEN FILTER MODULE FOR ALTERNATING FLOW FILTRATION

(75) Inventor: Jerry Shevitz, Livingstone, PA (US)

(73) Assignee: Repligen Corporation, Waltham, MA (US)

( * ) Notice: Subject to any disclaimer, the term of this patent is extended or adjusted under 35 U.S.C. 154(b) by 696 days.

(21) Appl. No.: 12/565,605

(22) Filed: Sep. 23, 2009

(65) Prior Publication Data

US 2010/0078395 A1    Apr. 1, 2010

Related U.S. Application Data

(60) Provisional application No. 61/099,633, filed on Sep. 24, 2008, provisional application No. 61/099,813, filed on Sep. 24, 2008.

(51) Int. Cl.
| | | |
|---|---|---|
| B01D 35/26 | (2006.01) | |
| B01D 29/13 | (2006.01) | |
| B01D 29/66 | (2006.01) | |
| B01D 35/30 | (2006.01) | |
| B01D 35/153 | (2006.01) | |
| B01D 29/11 | (2006.01) | |
| C12M 1/00 | (2006.01) | |

(52) U.S. Cl.
CPC .............. *B01D 35/30* (2013.01); *B01D 29/114* (2013.01); *B01D 29/66* (2013.01); *B01D 35/26* (2013.01); *B01D 29/13* (2013.01); *B01D 29/111* (2013.01); *B01D 35/153* (2013.01); *C12M 47/02* (2013.01)

(58) Field of Classification Search
CPC .... B01D 29/111; B01D 29/114; B01D 29/13; B01D 29/66; B01D 35/26; B01D 35/30; B01D 35/153; C12M 47/02
See application file for complete search history.

(56) References Cited

U.S. PATENT DOCUMENTS

| | | | |
|---|---|---|---|
| 2,751,084 A | 6/1956 | Wilhelm | |
| 4,256,583 A | 3/1981 | Lennartz | |
| 4,806,484 A | 2/1989 | Petrossian | |
| 5,106,501 A * | 4/1992 | Yang et al. | 210/266 |
| 5,563,068 A | 10/1996 | Zhang | |
| 5,811,259 A | 9/1998 | Hall | |
| 6,051,131 A | 4/2000 | Maxson | |
| 6,139,727 A | 10/2000 | Lockwood | |
| 6,544,424 B1 * | 4/2003 | Shevitz | 210/650 |
| 2003/0222006 A1 | 12/2003 | Cella | |
| 2010/0078395 A1 * | 4/2010 | Shevitz | 210/808 |

FOREIGN PATENT DOCUMENTS

| | | |
|---|---|---|
| EP | 0715875 | 6/1996 |
| WO | WO 2010/036338 A1 * | 4/2010 |

OTHER PUBLICATIONS

IPER of Nora Linder dated Mar. 29, 2011; Seven Pages.*
International Search Report for international application # PCT/US 09/05288, dated Mar. 29, 2011.

* cited by examiner

*Primary Examiner* — David A Reifsnyder
(74) *Attorney, Agent, or Firm* — Fish & Richardson P.C.

(57) ABSTRACT

Improved screen filter modules, related compartmentalized filtration modules, and related filtration processes, suitable for filtering fluid to eliminate suspended particulate matter, such as living cells or microcarriers anchoring living cells, or to separate particulate matter based on size. The improvement is the presence of a barrier that channels redirected filtrate to the portion of the filter most susceptible to clogging by the particulate matter and induces flow patterns that act against clogging.

22 Claims, 10 Drawing Sheets

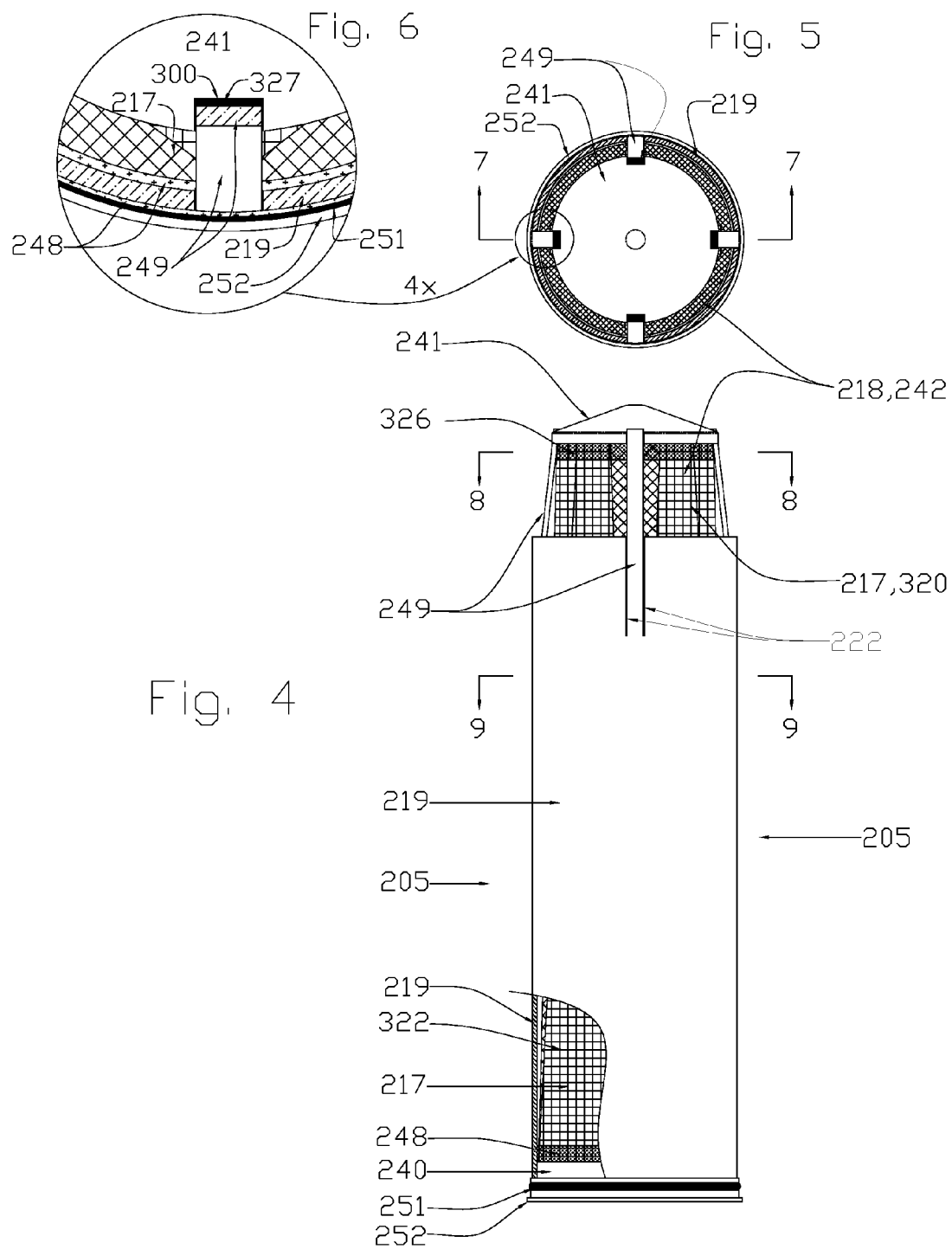

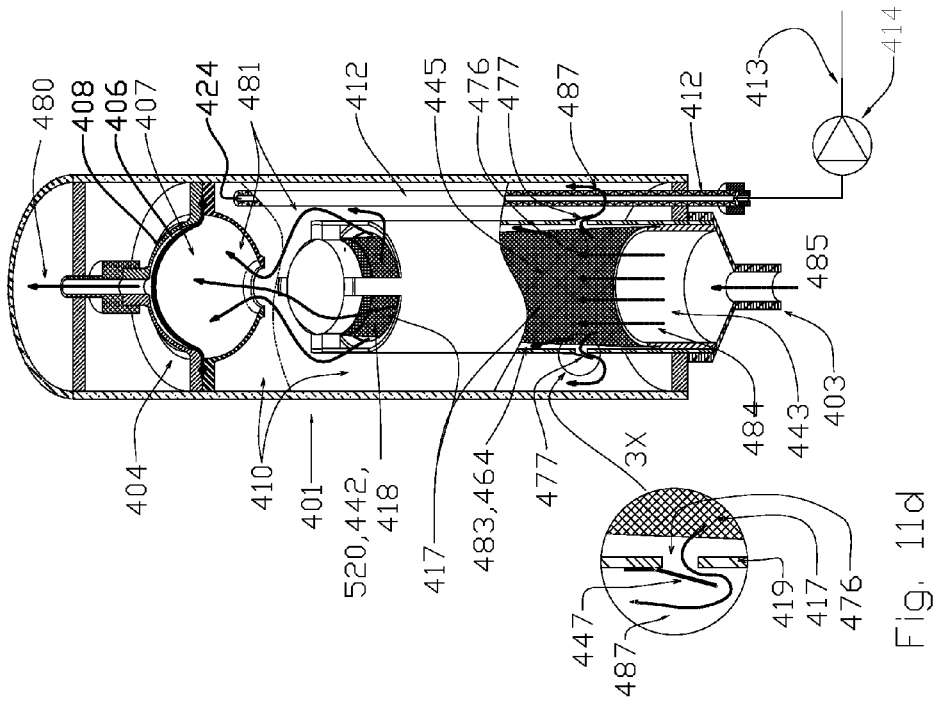
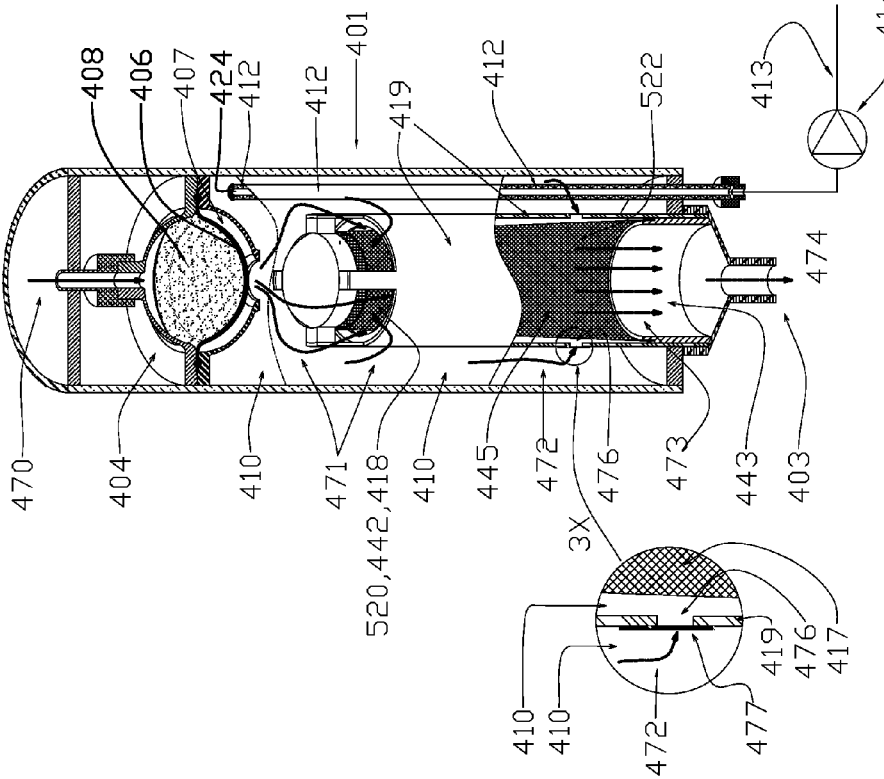

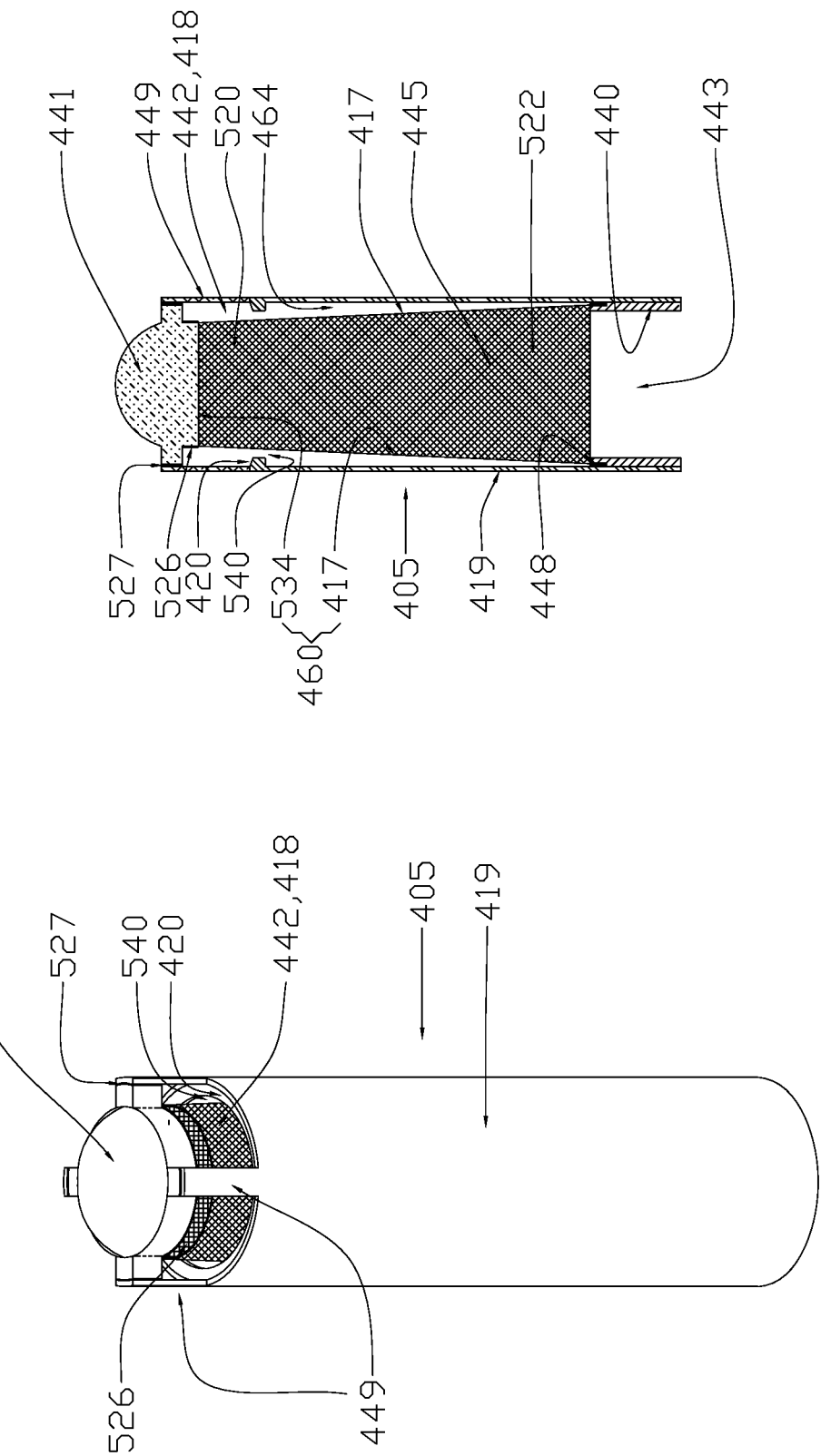

SCREEN FILTER MODULE FOR ALTERNATING FLOW FILTRATION

CROSS REFERENCE TO RELATED APPLICATIONS

This application claims the benefit of U.S. provisional application 61/099,633 filed Sep. 24, 2008 and U.S. provisional application 61/099,813 filed Sep. 24, 2008.

FIELD OF THE INVENTION

This invention relates to a device and methods for separating fluid from particulate matter such as living cells in suspension or attached to a solid matrix such as "microcarriers," or nonliving particles suspended in the fluid.

BACKGROUND OF THE INVENTION

Living cells suspended in fluid growth medium, for example in a bioreactor, have been used to generate pharmaceutically useful molecules. In many cases, the molecules produced by the cells are discharged into the growth medium; in other cases, the product is within the cells or may constitute the cells themselves; simultaneously, in search of increased productivity, the practice of cell culture has evolved. In one culture method, cells are grown in a continuous manner and to high concentrations by removing waste products from the culture and replacing with fresh media. In many cases, therefore, separation of cells from growth medium becomes an essential step in production of cell derived products. Separation of the molecules from the particulate cells in suspension or attached to microcarriers suspended in the growth medium can be achieved by a variety of methods. Not excluding other suspensions or solutions, the focus going forth will be on the use of anchorage dependent cells cultured on microcarriers. One separation method involves a "screen cage" with a mesh of pore size smaller than the microcarriers. The cage, in many cases, is placed in the culture vessel itself, and when appropriate, can be used to separate microcarriers from suspending medium, retaining the microcarriers within the vessel. The screen cage, while used in numerous processes, has a number of flaws, including that it is prone to clogging. Once clogged, it becomes useless and may result in premature termination of the production run at great cost and time loss. Furthermore, the volume of the internal screen cage reduces the capacity of the culture production vessel.

Another method, somewhat like an external screen cage or using a chamber and a partitioning screen, has been used for separation of microcarriers from culture medium. It involves continuous pumping of culture suspension through the screen. The screen retains the microcarriers and the media flows through. This device results in concentration of microcarriers within the separation chamber; however, while effective for short separation steps, it may result in entrapment of the microcarriers within the screened chamber causing its eventual clogging. Another limitation of this method, inherently results from the concentration of microcarriers with attached cells within the chamber during the separation process, a process that can deprive the cells of essential nutrients and lead to cell damage.

Another method for separating microcarriers from a culture medium involves a settling process, involving the of use of microcarriers, with attached cells, that together are heavier than the suspending medium. In a static culture, without agitation, the microcarriers, which are of specific gravity greater than the suspending medium, will settle to the bottom of the culture vessel, allowing removal of microcarrier-free medium from the top. While this method is reliable and commonly used, it is not preferred. The settling process is slow and time consuming, particularly at large scale, where settling distances are great. In addition, maintaining the cells in an unagitated environment can deprive the cells of oxygen and other nutrients. The current invention is designed to alleviate some of the limitations of other current systems.

The prior art provides filters that allows the molecules, but not larger particulate matter or cells to pass through it. In order to maximize the production of the molecules, systems have been developed to replenish the medium removed from the suspended entities during the filtration step. This has been achieved in the prior art using alternating tangential flow systems (See U.S. Pat. No. 6,544,424). The system described in that patent, however, are not well adapted to disposability nor does it provide a mechanism for controlling the flow dynamics across the filter surface that may enhance the capacity and efficiency of the filter. The use of a device that can controls the flow dynamics or patterns across the filter membrane may be used to enhance the effectiveness of the filter. The term filter includes, but is not limited to, any of ultrafiltration filters microfiltration filters, macrofiltration filters as well as screens. The ability to control the flow dynamics across a screen filter facilitates its use, as exemplified, in production of vaccines, a multistep process; examples of the steps include an initial wash of microcarriers, meaning rapid removal suspending media through the screen filter and retaining the microcarriers and replenishing removed media with fresh media. Such step may be repeated more than once; another step, follows steam sterilization of the suspended microcarriers, which also requires a rapid media exchange step, removing sterilization media and replacement with fresh growth media, so that the subsequent inoculation with cells will result in rapid attachment and growth of the cells on the microcarriers; a further step may include removal of growth media from the culture, retaining microcarriers and attached cells, followed by addition of a second, production, media and simultaneously inoculation with a virus; following viral growth phase, the virus laden cells may result in cell lysis; in which case, the screen filter may be used to separate and harvest the virus, retaining the microcarriers and cell remnants in the culture vessel. Facilitation of such multistep process by an efficient separation device such as described by the invention can greatly enhance the viral production process and making the process more efficient, reliable and cost effective. it would be desirable to have a less expensive system, preferably one that could be considered disposable. A disposable system would not have to be washed or prepared for use, time consuming efforts that decrease system reliability and increase operating costs It would also be simpler to dispose of and replace a spent system by an unused filter module as needed.

The present invention provides an enhanced screen filter module that can be used in a disposable manner if desired and an enhanced means for controlling the flow dynamics across a filter to enhance its filtration capacity and its usefulness in a greater range of applications.

BRIEF SUMMARY OF THE INVENTION

In its most general aspect, the invention is an improved screen filter module suitable for filtering fluid to separate suspended particulate matter, such as living cells or microcarriers anchoring living cells. The screen module is one adapted for use with an alternating pump that pulls the fluid through filter and then redirects a portion of the filtrate back through the filter. The module comprises a chamber within which, for example, particulate matter may be retained. The filter screen is part of the chamber wall. The improvement is the presence of a barrier that channels the redirected filtrate to the portion of the filter screen most susceptible to clogging by the particulate matter and generates flow dynamics within the filter chamber that inhibits clogging of the filter screen.

BRIEF DESCRIPTION OF THE DRAWINGS

FIG. 1a is a sectional view showing components and compartments of an assembled filtration module of the invention, also showing non-sectional views of portions of the assembly. The sectional view of the screen filter module within the compartmentalized filtration module is taken along the line 1-1 in FIG. 2.

FIG. 1b. Enlarged view of the indicated portion of FIG. 1a.

FIG. 2 is a side view of a screen filter module of the invention, which module is shown in section as part of a.

FIG. 4 is a side view of a screen filter module of the invention, which module employs a pleated screen filter.

FIG. 5 is a top view of the module shown in FIG. 4.

FIG. 6 is a 4× enlarged view of the indicated portion of FIG. 7.

FIGS. 11a and 11b are versions of FIG. 10 in which arrows describe flow patterns if fluid is present in the compartmentalized filtration module. FIGS. 11a and 11b show the flow patterns in opposite directions, depending on the force exerted by the alternating pump used in the compartmentalized filtration module.

FIG. 11c is an enlarged view of the indicated portion of FIG. 11a.

FIG. 11d is an enlarged view of the indicated portion of FIG. 11b.

FIG. 12. Isometric view of the screen filter module shown in FIG. 10.

FIG. 13. Sectional view of the screen filter module shown in FIG. 12.

DETAILED DESCRIPTION OF THE INVENTION

Figure 1:
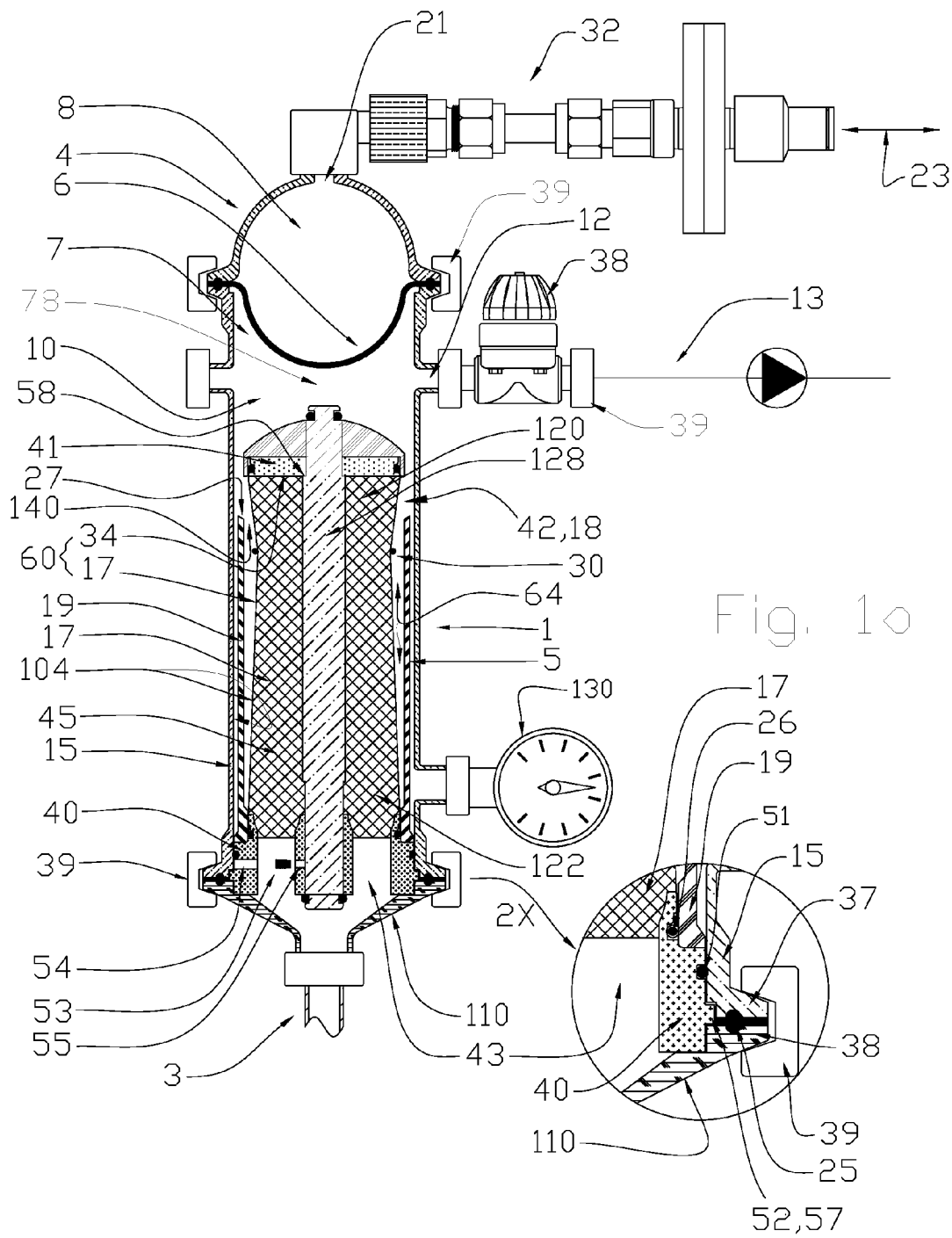

The invention has six general aspects:

In a first aspect, the invention is a screen filter module enhanced with an external barrier, the module comprising:

a) a retentate chamber, said chamber comprising a chamber wall and a chamber entrance, said chamber entrance permitting fluid containing suspended particulate matter (for example, fluid from a bioreactor) to enter or exit the chamber, and wherein the chamber wall comprises a filter screen, said screen comprising pores, such that said screen permits fluid and particles smaller than the pores but not suspended particulate matter larger than the pores to flow through it;

b) a barrier, said barrier positioned exterior to the retentate chamber so as to redirect fluid moving through the filter screen area proximal to the chamber entrance so that the redirected fluid moves towards a filter screen area more distal to the chamber entrance;

c) an exiting space between the filter screen and the barrier, said space for permitting fluid flow;

d) an opening between the filter screen and the perimeter of the barrier, said opening providing a means for fluid to leave the exiting space and escape the module; and e) an upper adapter for attachment to the (preferably tubular) filter screen (preferably at the upper end of said screen when said screen with its main axis vertically disposed), said adapter also attached to a rigid portion of the screen filter module, so as to prevent collapse of the filter screen.

In the first aspect of the invention, it is optional and preferable that the filter screen module further comprise a base adapter for attaching the barrier to the retentate chamber and/or anchoring the filter screen when used in a compartmentalized filtration module.

In a second aspect, the invention is a screen filter module enhanced with an internal barrier, the module comprising:

a) a filtrate chamber, said chamber comprising a chamber wall and a chamber entrance, said chamber entrance permitting fluid to exit or enter the chamber, and wherein the chamber wall comprises a filter screen, said screen comprising pores, such that said screen permits fluid and particles smaller than the pores but not suspended particulate matter that is larger than the pores, to flow through it;

b) a barrier, said barrier positioned inside the filtrate chamber so as to redirect filtrate chamber fluid moving towards a filter screen area distal to the filtrate chamber entrance so that the redirected fluid moves within the filtrate chamber towards a filter screen area more proximal to the filtrate chamber entrance and exits the filtrate chamber so as to flow into the retentate chamber;

c) an opening in said barrier to allow limited fluid flow through the barrier;

d) a bypass space between said barrier and the filtrate chamber wall, said space for permitting fluid entering the filtrate chamber through the filter screen to bypass the barrier and flow to the filtrate chamber exit; and e) a lower adapter attached to the filter screen.

In the second aspect of the invention, it is optional and preferable that the filter screen module further comprise a base adapter for attaching the barrier to the filtrate chamber and/or anchoring the screen filter module when used in a compartmentalized filtration module.

In a third aspect, the invention is a compartmentalized filtration module (also referred to herein simply as a "filtration module") that contains a screen module enhanced with an external barrier such that the screen filter module comprises a retentate chamber, the filtration module comprising:

a) a retentate chamber, said retentate chamber comprising a retentate chamber wall and a retentate chamber entrance, said entrance permitting fluid containing suspended particulate matter to enter and exit the chamber, said retentate chamber wall comprising a filter screen, said screen comprising pores, such that said that said screen permits fluid and particles smaller than said pores but not suspended particulate matter larger than the pores to flow through it;

b) a filtrate chamber adjoining said retentate chamber, said filtrate chamber comprising a filtrate chamber wall and a filtrate chamber entrance, said filtrate chamber wall comprising the filter screen also comprised by the retentate chamber wall, said filtrate chamber entrance permitting fluid to enter or exit the filtrate chamber;

c) an alternating pump connected to the filtrate chamber entrance, said pump for pumping fluid in alternating directions through the filtrate chamber entrance and thereby for pumping fluid in alternating directions through the filter screen;

d) a barrier, said barrier positioned inside the filtrate chamber so as to redirect fluid moving through the filter screen area proximal to the retentate chamber entrance so that the redirected fluid moves towards a filter screen area more distal to the retentate chamber entrance;

e) an exiting space between the filter screen and the barrier, said space for permitting fluid flow;

f) an opening between the filter screen and the perimeter of the barrier, said opening providing a means for fluid to escape the exiting space and the retentate chamber;

g) an upper adapter for attachment to the (preferably tubular) filter screen (preferably at the upper end of said screen when said screen with its main axis vertically disposed), said adapter also attached to a rigid portion of the screen filter module, so as to prevent collapse of the filter screen; and h) a harvest port for removing fluid from the filtrate chamber.

In the third aspect of the invention, it is optional and preferable that the filter screen module further comprise a base adapter for attaching the barrier and/or anchoring the filter screen module in the compartmentalized filtration module.

In a fourth aspect, the invention is a compartmentalized filtration module that contains a screen filter module enhanced with an internal barrier such that the screen filter module functions as the filtrate chamber, the filtration module comprising:

a) a retentate chamber, said retentate chamber comprising a retentate chamber wall and a retentate chamber entrance, said entrance permitting fluid containing suspended particulate matter to enter and exit the chamber, said retentate chamber wall comprising a filter screen, said screen comprising pores such that said screen permits fluid and particles smaller than said pores but not suspended particulate matter larger than said pores to flow through it;

b) a filtrate chamber adjoining said retentate chamber, said filtrate chamber comprising a filtrate chamber wall and a filtrate chamber entrance, said filtrate chamber wall comprising the filter screen also comprised by the retentate chamber wall, said filtrate chamber entrance permitting fluid to enter or exit the filtrate chamber;

c) an alternating pump connected to the filtrate chamber entrance, said pump for pumping fluid in alternating directions through the filtrate chamber entrance and thereby for pumping fluid in alternating directions through the filter screen;

d) a barrier, said barrier positioned inside the filtrate chamber for redirecting fluid moving towards a filter screen area distal to the filtrate chamber entrance so that said redirected fluid moves through the filter screen area more proximal to the filtrate chamber entrance;

e) a bypass space between said barrier and the filtrate chamber wall, said space for permitting fluid entering the filtrate chamber through the filter screen to bypass the barrier and flow to the filtrate chamber entrance;

f) an opening in said barrier to allow limited fluid flow through the barrier;

g) a lower adapter for attachment to the filter screen, said adapter also attached to a rigid portion of the filtration module, so as to prevent movement of the filter screen; and h) a harvest port connected to said alternating pump, said port for removing fluid pumped from the filtrate chamber.

In the fourth aspect of the invention, it is optional and preferable that the compartmentalized filtration module further comprise a base adapter for attaching the barrier to the filtrate chamber and/or anchoring the screen filter module in the compartmentalized filtration module.

In a fifth aspect, the invention is a process for removing particulate matter from a fluid in which it is suspended, the process being an example of one that utilizes the screen filter module enhanced with an external barrier, the process comprising the steps of:

a) feeding a suspension into a retentate chamber via an entrance in that chamber, said entrance being the retentate chamber entrance, said suspension comprising the particulate matter suspended in the fluid, said retentate chamber connected to a filtrate chamber via a shared filter screen in their respective walls, said filter screen comprising pores of a size that allow the fluid and particles smaller than the screen pores but not the suspended particulate matter that are larger than the screen pores to pass through, said filtrate chamber comprising an entrance connected to an alternating pump;

b) directing the suspension at the filter screen so that fluid but not said suspended particulate matter passes through the filter screen, said directing achieved by the action of the alternating pump;

c) collecting, in the filtrate chamber, the fluid that passed through the screen filter, said collected fluid being the filtrate fluid;

d) removing a portion of the filtrate fluid from the filtrate chamber, thereby leaving unremoved filtrate fluid in the filtrate chamber;

e) directing the unremoved filtrate fluid back at the screen filter, such filter screen directing achieved by the alternating pump exerting a force on said unremoved filtrate fluid, such that a barrier redirects filtrate fluid moving towards a filter screen area proximal to the retentate chamber entrance so that the redirected fluid moves towards a screen filter area more distal to the retentate chamber entrance; and f) repeating steps (a) through (e).

In a sixth aspect, the invention is a process for removing particulate matter from a fluid in which it is suspended, the process being an example of one that utilizes the screen filter module enhanced with an internal barrier, the process comprising the steps of:

a) feeding a suspension into a retentate chamber via an entrance in that chamber, said entrance being the retentate chamber entrance, said suspension comprising the particulate matter suspended in the fluid, said retentate chamber connected to a filtrate chamber via a shared filter screen in their respective walls, said filter screen comprising pores, said pores of a size that allow the fluid and particles smaller than the pores but not the suspended particulate matter that are larger than the screen pores to pass through, said filtrate chamber comprising an entrance connected to an alternating pump;

b) directing the suspension at the screen so that fluid but not said suspended particulate matter passes through the filter screen, said directing achieved by the action of the alternating pump;

c) collecting, in the filtrate chamber, the fluid that passed through the filter screen, said collected fluid being the filtrate fluid;

d) removing a portion of the filtrate fluid from the filtrate chamber, thereby leaving unremoved filtrate fluid in the filtrate chamber;

e) directing the unremoved filtrate fluid back at the screen filter, such directing achieved by the alternating pump exerting a force on said unremoved filtrate fluid, such that a barrier redirects fluid moving towards a screen filter area distal to the filtrate chamber entrance so that the redirected fluid moves towards a screen filter area more proximal to the filtrate chamber exit; and f) Repeating steps (a) through (e).

In the sixth aspect of the invention, a portion of the fluid (preferably less than 50 percent, more preferably less than a third) is permitted to flow through the barrier which may have small openings.

As can be seen from the modules exemplified in the drawings, it is preferable that the filter screen be elongated in the direction of its main axis and be symmetrical as possible around that axis.

The materials used to make the filter screen module and the compartmentalized two-chamber module are preferably synthetic polymers or plastics so as to reduce material and production cost relative to a metal construction and make it more economical to treat it as a disposable module. Preferred plastic for the filter module body are polysulfone, polycarbonate, kynar and others, and for the base adapter, barrier, and upper adapter they are: polysulfone, polycarbonate, kynar and others, and the screen material they are: polyester, PVDF, Kevlar and others; preferably such plastics are high performance capable of withstanding steam sterilization or sterilization by other means.

The filter screen is preferably made of pores separated by the minimal amount of plastic required for structural integrity and stability. The filter screen will most likely correspond to a foldable, collapsible mesh whose collapse is prevented in the module because of the rigid support provided by other portions of the module to which the mesh is adhered to.

Pore sizes capable of preventing passage of living animal cells or microcarriers generally range, respectively, from 0.1 micron to 80 microns. Spherical microcarriers typically have a diameter in the range 100 to 500 microns, so the pore size will have to be less than the microcarrier diameter used. The pores normally required in such case is about 75 micron in order to allow desired molecules, present in the fluid, to pass through the filter but not the larger microcarriers. Examples of desired molecules are antibodies, viruses, and other pharmaceutically active molecules. The minimum size will depend on that needed to allow the molecules to pass through the filters. The molecules will be those that were produced by the living cells, and therefore normally be smaller than the cells or microcarriers.

The pore size can also be chosen to allow particles of a larger size to be separated from particles of a smaller size.

The screen filter module is preferably used with aqueous fluids, usually enhanced with regard to pH, salts and nutrients as needed for living cells.

Sterilization of the screen filter module prior to use can be achieved by autoclaving or other forms of steam sterilization or sterilization by radiation or by chemical means. Sterilization of the compartmentalized filter module can be achieved by similar means. When using plastic materials, the components can, where necessary, be caused to adhere to each other using adhesives such as high temperature epoxies, cyanoacrylates, heat, mechanical coupling, ultrasonic welding, or solvents. The surface area of the filter screen is based on application and volume of culture to be processes, and is preferably in the range between 10 and 10,000 $cm^2$. The length, diameter and configuration of the screen are not limited but may vary considerably based on application.

The filter screen may be tapered, so that, in the first aspect of the invention, for example, its attachment diameter at the point it meets the module's upper adapter is smaller than the attachment diameter where it meets to the lower scaffold perimeter.

When the module is part of a compartmentalized filter module of this invention, the entrances of the two chambers and the alternating pump are preferably aligned along the main axis of symmetry of the screen filter module.

When the barrier is external to the filter screen, it preferably redirects fluid away from portion of the filter that extends from the filter entrance almost the entire length of the filter (preferably at least 50 percent (more preferably at least 70 percent) of the entire length, preferably not more than 99 percent of the entire length) towards where it meets the upper adapter.

The scaffold element is a structural component that is added to prevent collapse of the filter screen and/or its movement when subjected to fluid moving under pressure. For screen filter modules which are intended to be used while vertically disposed with the retentate chamber entrance at the lower end, the upper end of the filter screen (along with the attached upper adapter) would collapse under the force of gravity or stress created by the alternating flow, absent a scaffold element. The scaffold element in that case is preferably linked to the portion of the filter screen most distal to the chamber entrance (i.e., the higher end of the filter screen) to the surrounding barrier. The scaffold element may be attached directly to the filter screen or, preferably, indirectly by virtue of being attached to the upper adapter which in turn is attached to the filter screen. The scaffold element may be an extension of the barrier, and to some extent will therefore affect fluid flow but that is not its primary function.

When the barrier is internal to the screen filter as in the second, fourth and sixth aspects of the invention, the screen filter module may be attached at its entrance end to the outer perimeter of the pump fluid chamber outlet. The other end of the module may be attached to a lower adapter. The lower adapter in turn is fixed within the filtration module by its attachment to the filtration module wall with a high strength bridge or link, preferably wire or thread that will not interfere with movement of retentate within the filtration module chamber.

In addition to the advantages described above for the current invention, the invention is designed to allow or perform rapid separation steps of microcarriers or other particles from their suspending medium, as required in some production processes. It is also designed to allow rapid and continuous reversible flow of cells growing attached to the microcarriers between the culture vessel and filtration modules resulting in removal of cells from the culture vessel for only a short time, followed by the rapid return of the cells to the culture vessel where the cells are nourished. The reversible flow allows rapid equilibration of the content in the culture vessel with the culture in the filtration module, keeping the cells nourished and in good condition during the filtration process. As there may be several filtration steps during a production process, which may include several manipulations of the cultured cells, it is essential that the cells be maintained in optimally viable conditions during the filtration steps. Damaging the culture during any of the steps may be detrimental to the remainder of the production process.

The inventions may be further understood by reference to the attached Figures.

Figure 10:
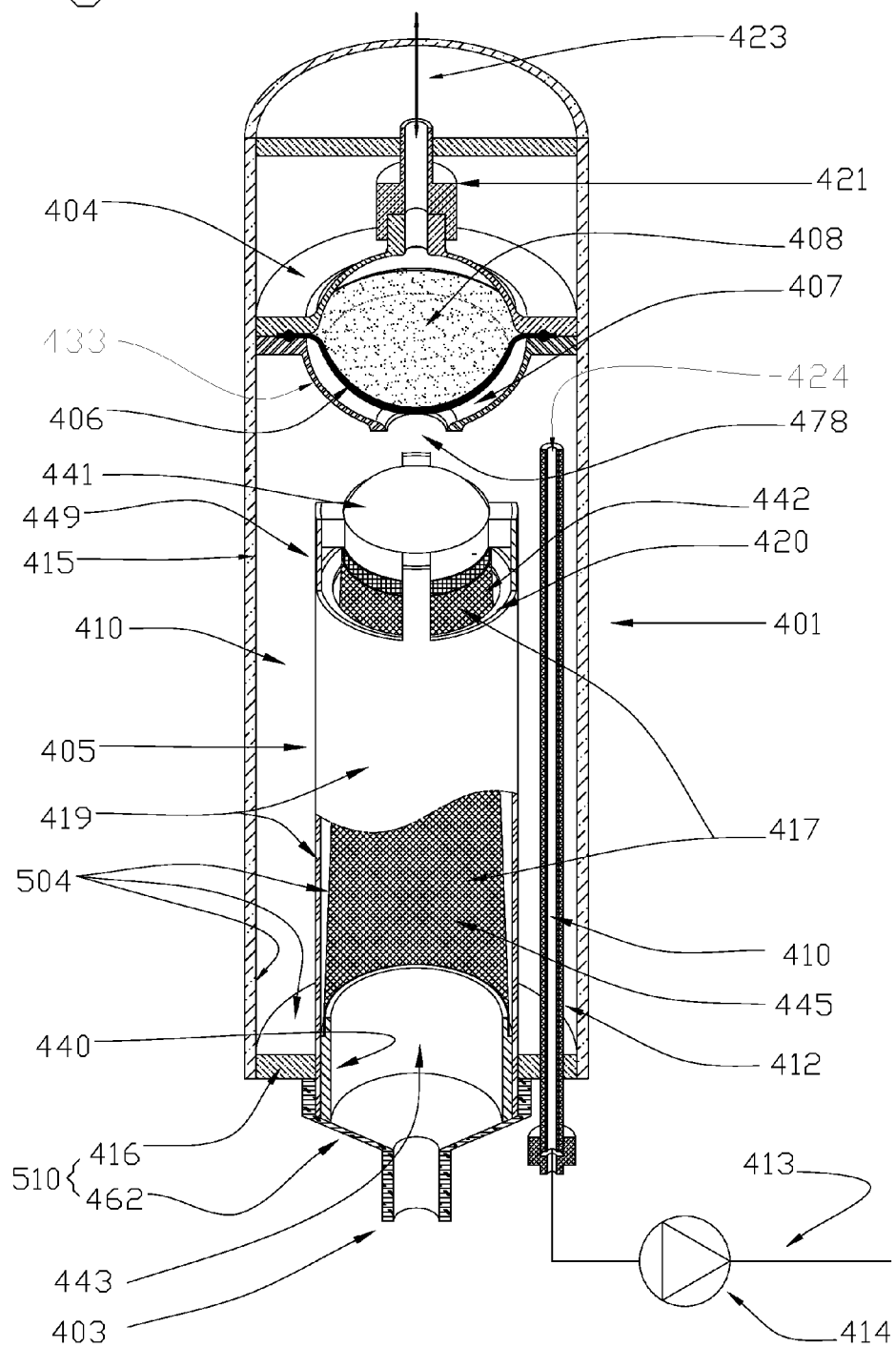
FIG. 10 is a partial sectional view of a compartmentalized filtration module of the invention.

FIG. 10 illustrates a compartmentalized filtration module 401 that comprises a screen filter module 405. The compartmentalized filtration module 401 is an example of the third aspect of the invention and the screen filter module 405 is an example of the first aspect of the invention.

FIG. 12 shows a center isometric view of the screen module 405 of FIG. 10. FIG. 13 shows a fully cross-sectional view of the screen module 405. FIG. 12 and FIG. 13 together show that the screen filter module 405 is an example of the first aspect of the invention. The module comprises a retentate chamber 445, a chamber wall 460, a chamber entrance 443, and a filter screen 417 that is part of the chamber wall. The chamber wall 460 comprises the screen filter 417 and a surface 534 of the upper adapter 441. The module also comprises a barrier 419 exterior to the chamber 445 and further comprises an exiting space 464 between the screen filter 417 and the barrier 419. The screen filter 417 adheres to upper adapter 441 by mechanical means (FIG. 10) via an adhesive layer 526 (FIG. 12; see also FIGS. 4, 6, 7 and 13) or by other means. The upper adapter 441 is attached to the barrier 419 be means of fasteners, other mechanical means, heat, ultrasonic welding or adhesives; shown is attachment with a glue layer 527 and barrier adapter posts 449 that are part of the barrier 419 and that fit into the scaffold post receptacles (as shown for receptacles 300 in FIG. 6) that are part of the upper adapter 441. At the other end of the module, the screen and barrier are attached to the screen filter module base adapter 440, ("also referred to as the "lower screen adapter") the screen 417 by adhesive layer 448, although other means of attachment are possible. Together, the upper adapter 441, the base adapter 440, the barrier 419, and barrier adapter posts 449 provide support for the screen filter 417, allowing it to be firmly stretched between the adapters 440 and 441. The screen thus fixed at both ends to respective adapters 440 and 441 is firmly positioned, preventing its collapse during the stresses of the filtration process. The width of posts 449 is selected to optimize flow between retentate and filtrate chambers. Also considered in selecting the width of the posts is their indicated use as means of attaching adapter 441 with the attached screen 417 to the barrier body, where the width affects the flexibility of the post. Attachment of the post 449 to upper adapter 441 with a slight inward, (towards the center axis of the module), bend or tension so as to force the attached adapter 441 upward; thereby puling the attached screen 417 upward, maintaining it taught. The overcut 222 (lower portion of post 249), shown in FIG. 4, is designed to add flexibility to the post and to increase the range of bending.

In FIG. 13, the majority of the fluid directed at the area 522 of the screen proximal to the retentate chamber entrance 443 will be redirected to the area 520 of the filter screen that is more distal to the retentate chamber entrance 443.

In FIGS. 12 and 13, it can further be seen that, between the filter screen 417 and the inner perimeter the restrictive platform 420, (and therefore effectively between the filter screen 417 and the barrier 419) there is an opening 540. The presence of the restrictive platform 420, which is part of the barrier 419, directs fluid, flowing from the pump exit end 478 (See FIG. 10) into the filtrate compartment 410 ("compartment" and "chamber" are used interchangeably herein), into the retentate compartment 445, through the upper area 418 of the screen 417 and restricts the fluid flow that otherwise would go into exiting space 464 between the screen 417 and the barrier 419, areas of the screen that are more proximal to the retentate entrance opening 443.

The filter screen 417 will be porous, so as to allow fluid and particles smaller than the screen pores to pass through it. However, pores of the filter will be sufficiently small to retain and prevent suspended particulate matter larger than the screen pores to leave the chamber 445.

FIG. 10 shows a view of the compartmentalized filtration module 401 that comprises a screen filter module 405. FIG. 10 is a center isometric sectional view except for part of the screen filter module 405. The screen filter module 405 is shown in a partially sectional isometric view that can be further understood from FIGS. 11a, 11b, 12 and 13. The compartmentalized filtration module 401 is essentially symmetrical around its longitudinal axis. (The harvest port 412 is, however, shown while only at one position is not limited to its length or configuration, nor are the numbers and positions of the post limited; preferably, harvest port opening 424 is positioned above the screen, such that when harvesting from the harvest port, removing air from the system and displacing it with liquid from the culture vessel flowing into the filtration module through the screen, thus immersing the screen in liquid and assuring full flow across the exit end 442 and upper screen area 418, between retentate and filtrate compartments, 445 and 410, respectively).

In FIG. 10, the compartmentalized filtration module 401 comprises not only the screen filter module 405, but also a filtrate chamber 410. The filtrate chamber is enclosed by a filtrate chamber wall 504 that comprises the outer filtrate chamber wall 415 the base adapter plate 416 the filter screen 417 and an upper wall formed by the pump housing 404, and specifically its external wall 433. Accordingly, the filter screen 417 is part of both the filtrate chamber wall 504 and the retentate chamber wall 460 (See FIG. 13).

FIG. 10 also shows the alternating pump 404 which is connected to the filtrate chamber entrance 478 which, depending on the direction of fluid flow, can also function as the filtrate chamber exit. Here chamber entrance/exit 478 is also the pump opening through which fluid is exchanged between the pump and the filtrate chamber. The pump 404 comprises a fluid pump chamber 407, an air pump chamber 408, and a diaphragm 406 separating the fluid pump chamber 407 and the air pump chamber 408. An air inlet assembly 421 that alternately directs compressed air into chamber 408 or exhausts that chamber is also shown connected to the pump 404.

Further evident in FIG. 10 is a base adapter 510 which comprises an adapter plate 416 and a conical adapter 462. The conical nature of the adapter inhibits settling of microcarriers on the adapter surface and facilitates their flow towards the fluid connector 403 through which fluid can flow from the retentate chamber entrance 443 to the culture vessel followed by flow from the culture vessel in the reverse direction.

Figure 16:
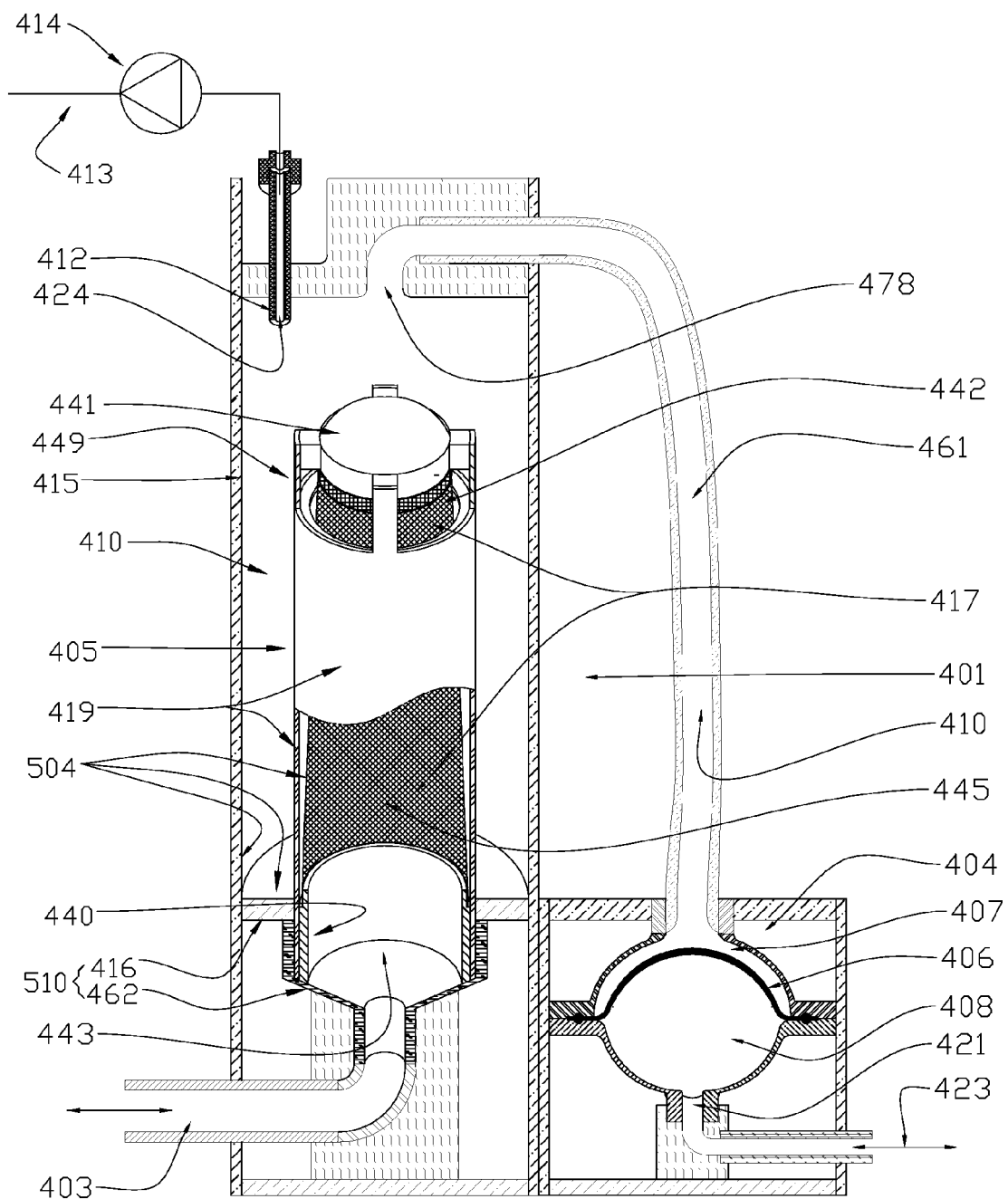
FIG. 16. Variation of invention shown in FIG. 10.

In FIG. 10 the alternating pump 404 is connected directly to the filtrate chamber 410. In a variation of the aspect of the invention illustrated in FIG. 10, the alternating pump is connected to the filtrate chamber by an intervening conduit 499 as shown in FIG. 16.

Fluid flow across the filter screen 417 can be initially primed by activation of harvest pump 414 and removing air, through lines 412 and 413, from the filtration module 401, replacing air with liquid, flowing into the filtration module 401 through fluid connector 403, which is connected at its other end to the culture container (not shown). Filling retentate chamber 445 with unfiltered retentate fluid, followed by flow into the filtrate chamber 410 into across screen 417, filling both chambers and immersing barrier and screen in fluid so there is fluid contact between the chambers. Pressure on either the fluid within the chamber 445 or the fluid exterior to the chamber can be exerted by an alternating pump to move fluid through the filter screen. But the pores of the filter will be sufficiently small to prevent the suspended particulate matter larger than the screen pores to leave the chamber 445, these capabilities in combination with harvesting liquid and particles smaller than the screen pores can be used to isolate small molecules that pass through the filter with the fluid or alternatively, by elimination of fluid from the chamber 445, to isolate the particulate matter in more concentrated form.

The restrictive platform 420, the screen exit end 442, and the barrier adapter posts 449, can be understood by reference to FIGS. 12 and 13 and the related descriptions.

FIGS. 11a and 11b show the same compartmentalized filtration module 401 as is shown in FIG. 10, but shows how the direction of fluid flow is changed by the action of the pump 404.

In FIG. 11a, flow line arrows 470 shows air flow direction into the pump chamber 408, pressurizing that chamber and forcing diaphragm 406 to expand into chamber 407, forcing fluid from that chamber. Flow lines, 471, 473 and 474 illustrate one flow pattern for fluid directed by the pump 404 from the filtrate chamber 410 at the filter screen 417 is forced to flow to a filter screen exit end 442 (corresponding also to upper screen area 418), which exit end is distal to the retentate chamber entrance 443. Flow thus generated will dislodge microcarriers or particulates attached to the corresponding, retentate chamber wall or inner screen wall 417. The microcarriers thus dislodges will be diluted by the inflow of filtrate and forced to flow from the exit end 442 towards the entrance end 443 and back to the main culture via the fluid connector 403. Absent the barrier 419, the fluid emerging from pump 404 will flow from the filtrate side into the retentate side across the screen uncontrolled or directed. The flow across the screen may occur anywhere along the screen including predominantly at its base adjacent to the entrance 443, which may in fact be the path of least resistance. Such flow would result in retaining microcarriers at increased concentration towards the distal end of the filter. Subsequent cycles of the pump and continued return of filtrate at the proximal end of the filter, at the entrance 443 side will further accumulate microcarriers at the distal end, which may eventually clog the screen. Continued removal of filtrate from the filtrate chamber 410 will add to the above indicated concentrating effect on the microcarriers.

In FIG. 11b, flow line arrows 480 shows the exhaust of pump chamber 408 forcing diaphragm to move into the exhausted space of that chamber and inversely causing pump chamber 407 to expand and fill with the filtrate fluid. Arrows 481, 484, 485, and 487 illustrate a second flow pattern for fluid directed by the pump 404 in a direction from the retentate chamber entrance 443, into the retentate chamber 445, through the filter screen 417 through filter exit end 442 and upper screen area 418, into filtrate chamber 410. The flow is completed by pump 404 return of the filtrate into pump chamber 407. Noting the flow in this direction, towards the pump, it is preferable to have the flux of fluid flow from the retentate chamber to the filtrate chamber more uniformly distributed across the entire surface of the screen so as to minimize localized concentration of microcarriers within the filter module. More preferable, is that any concentration of microcarriers occur proximal to the entrance end 443 of the filter, to facilitate the return of microcarriers to the main culture vessel through fluid connector 403.

To facilitate objectives described in the above paragraph, secondary barrier openings 476 and a one directional check valves 477 are used. In the flow shown in FIG. 11b, check valve 477 permit a fraction of the total fluid flow across screen 417 (see enlarged view FIG. 11d) through barrier opening 476 from the proximal region to the entrance end 443 of the filter into filtrate compartment 410; thereby, reducing the concentrating microcarriers at filter distal end. Flow across the screen into exiting space 464 facilitates this process. (This is further emphasized in FIG. 1a, by use of a constrictive "O" ring 30 around the screen 17 to permit greater unrestricted flow from the proximal end (proximal to entrance 43) of the retenate compartment to the filtrate compartment and through space 64.) On the reverse flow shown in FIG. 11a, check valve 477 blocks flow through openings 476, forcing the flow from the filtrate compartment to the retentate compartment through upper screen area 418 and adjacent screen region. These secondary barrier openings are optional and the degree of flow they allow when present does not change the fact that in FIG. 11, the majority of the fluid directed at the area 522 of the filter screen proximal to the retentate chamber entrance 443 will be redirected to an area 520 of the filter screen that is more distal to the retentate chamber entrance 443.

Also evident in FIGS. 11a and 11b are the filtrate chamber 410, and the retentate chamber 445. Fluid flows from the retentate chamber into the filtrate chamber and then via the harvest port 412, harvest pump 414, and harvest line 413 for collection and/or further processing.

FIGS. 4 through 9 together show a pleated version of a screen filter module 205 that is an example of the first aspect of the invention. FIG. 4 is a side view except that part of that view, at the lower left, shows a side view with a portion of the barrier 219 absent. Without the barrier, the filter screen 217, the adhesive layer 248, and lower screen adapter (also a base adapter) 240 are visible.

Figure 2:
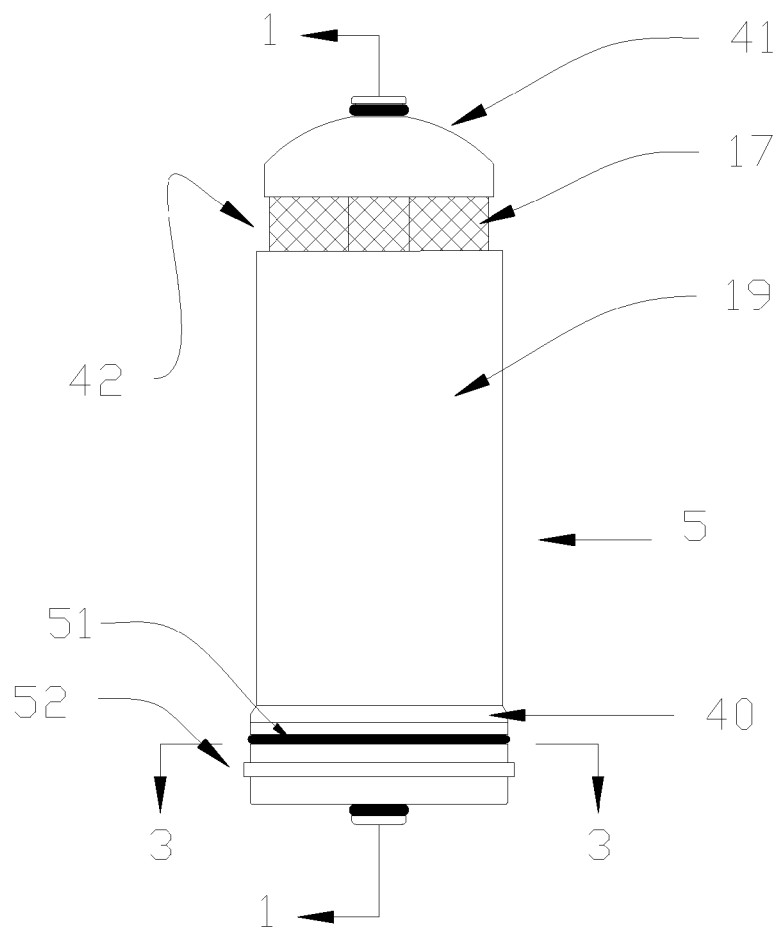
Figure 3:
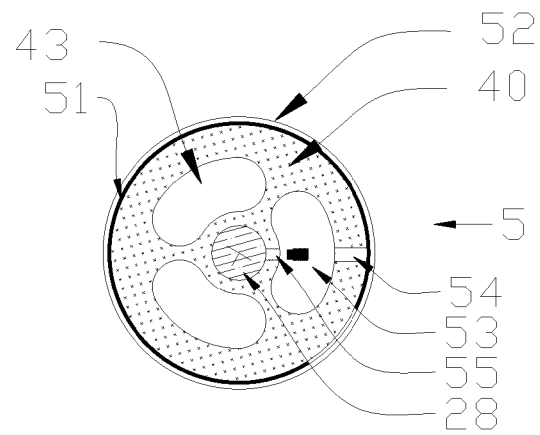
FIG. 3 is a sectional view of the screen filter module shown in FIG. 2, taken along the line 3-3 in FIG. 2.

FIG. 4 shows a view of a version of the screen filter module 205 that contains a step 252 that is part of the lower screen adapter 240. A similar step 52 that is part of the lower screen adapter 40 is shown in FIGS. 1 and 2; its insertion into a counterpart receptacle 57 facilitates positioning and securing the screen filter module in a compartmentalized filter module (such as in FIG. 1 where the step 52 facilitates insertion into a receptacle (socket) defined by the outer filtrate chamber wall 15 and the base adapter 110.) An O-ring 251 (51 in FIGS. 1 and 2) that encircles the lower screen adapter 240 (40 in FIGS. 1 and 2) seals the lower screen adapter against the filter housing thus effectively preventing leakage of retentate into the filtrate compartment.

Figure 8:
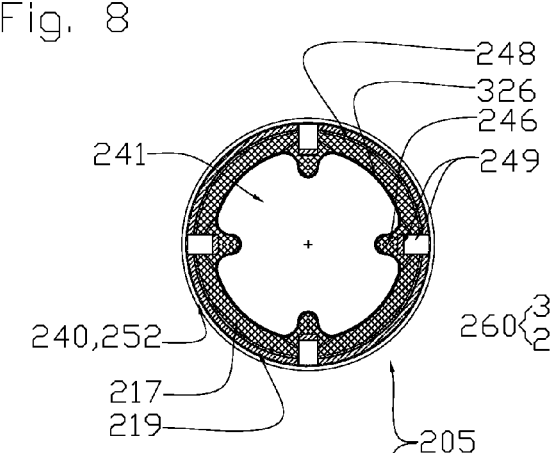
FIG. 8 is a sectional view of the screen filter module shown in FIG. 4, taken along the line 8-8 in FIG. 4.
Figure 9:
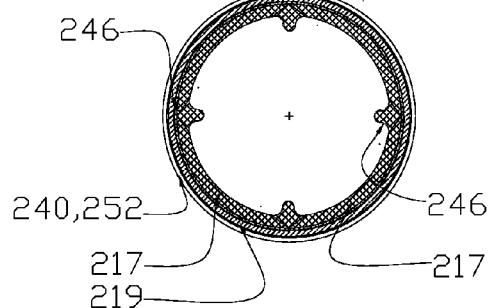
FIG. 9 is a sectional view of the screen filter module shown in FIG. 4, taken along the line 9-9 in FIG. 4.
Figure 7:
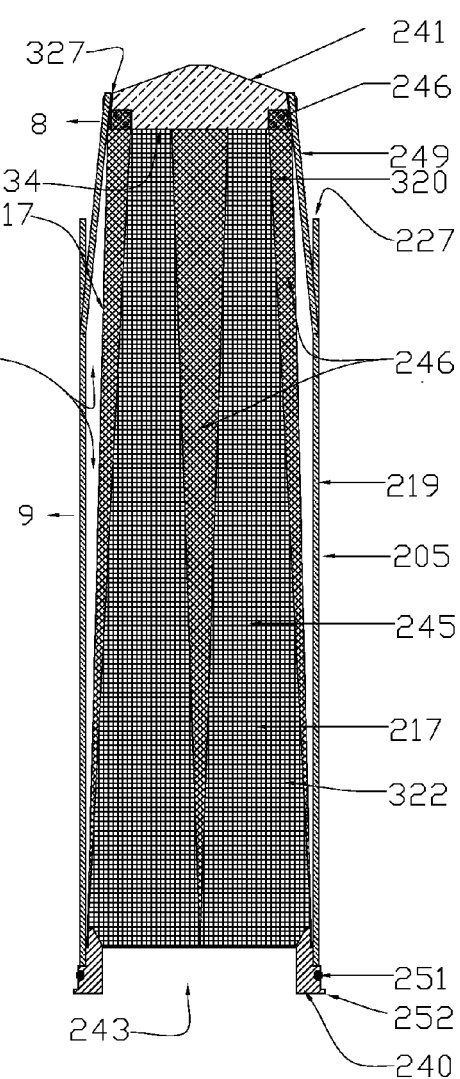
FIG. 7 is a sectional view of the screen filter module shown in FIGS. 4 and 5, the view taken along the line 7-7 in FIG. 5.

The pleated version of the screen filter module 205 shown in FIGS. 4 through 9 can be used the same as the screen filter modules shown in FIGS. 1a, 1b, and 10 through 13 and used in the compartmentalized filtration module 401 in a manner shown in FIGS. 1, 10 and 11. The lower screen adapter 240 and the O-ring 251, shown in FIGS. 4 and 7, can be fitted into a housing similar to 415 in FIG. 10 to form a fluid tight seal. The actual screen module shown in FIG. 10 is, however, secured to base 510. Cross-sectional views FIGS. 8 and 9 show where the filter screen 217 has been gathered to form four pleats 246. How the pleats 246 increase in size as one proceeds from the base to the top of the filter screen module is show not only by comparing FIG. 8 to FIG. 9, but by viewing FIG. 7. While four pleats are shown, it is obvious that more or less pleats can be used, the depth of the pleats varies as well as their configuration.

Evident in the module illustrated in FIGS. 4 through 9 are the barrier adapter post 249 (also referred to as a scaffold element), the upper adapter 241 (also referred to as the scaffold adapter), the pleats 246, the barrier 219 and the perimeter 227 of the barrier 219. The scaffold adapter 241 is attached to the barrier 219 by means of barrier adapter posts 249 that are part of the barrier itself, where the posts fit into and are pinned or glued 327 to the scaffold post receptacles 300 that are part of the scaffold adapter 241. Together, the upper adapter 241 and the barrier 219 provide support for the filter screen 217, preventing its collapse during the filtration process.

Also evident in the module illustrated in FIGS. 4 through 9 are the retentate chamber 245, upper screen area 218, exiting space 264, retentate chamber entrance 243, and retentate chamber wall 260. The chamber wall 260 comprises the filter screen 217 and a lower surface 334 of the upper adapter 241 and inner surface of lower screen adapter 240. In FIG. 4 adhesion layer 326, attaching the screen to the upper adapter 241, and adhesion layer 248, attaching screen 217 to lower screen adapter 240, are shown.

FIGS. 1a, 1b, 2 and 3 together show another example of a reusable screen filter module 5 that is a first aspect of the invention as well as a compartmentalized filtration module 1 that utilizes filter module 5. FIG. 1a shows a filtration module that can be assembled or disassembled, noting the reversible "S" line sanitary connections, as common in the industry. Also shown are: fluid connector 3, alternating pump 4, 6, fluid chamber 7, air pump chamber 8, harvest line 13, and sanitary connections and clamp 39 between parts; noting further, the sanitary gasket 25 used in such connections, including two adjacent flanges 37 and 38 and a clamp 39 to seal the flanges against the gasket to secure the seal. FIG. 1a also shows filtrate chamber 10, an, outer filtrate chamber wall 15, barrier 19, perimeter 27 of the barrier 19, filter screen 17, upper area 18 of the screen, air inlet adapter 21, exit end 42, retentate chamber entrance 43, retentate chamber 45, O-ring 51, step 52, surface 34 of the upper adapter 41, the retentate chamber wall 60, exiting space 64, filtrate chamber entrance 78 (which overlaps with fluid chamber 7 and is not limited to the size shown) and the base adapter 110, area 120 of the filter screen that is more distal to the retentate chamber entrance 43, and area 122 of the screen proximal to the retentate chamber entrance 43, opening 140 between the barrier perimeter 27 and the screen 17, filtrate chamber wall 104 and the harvest port 12.

Also shown in FIGS. 1a, 1b, 2 and/or 3 are a center post 128 that is connected to and supports the upper and lower screen adapters, 41 and 40, respectively, where ledge 58 in post 128 upholds adapter 41 from sliding down and a pin or set screw 53 secures post 128 to the lower screen adapter 40. Opening 54 in adapter wall 40 provides access to the set screw with a wrench or a tool for maneuvering the screw or pin 53 into opening 55 and forcing the screw against post 128 to secure its position against the lower adapter 40. Noting "O" ring 26, to which one end of the screen is mechanically attached, by sewing or other means, The "O" ring, in turn is mechanically secured against the base adapter 40, also by common means; similar attachment of an "O" ring to the second end of the screen and their attachment to the upper adapter 41 is achieved; thereby, having the ability to slide adapter 40 against post 128 and securing the two adapters with screw 53 allows extension of the screen 17 between the two adapters and keeping it taught. Also shown is a pressure meter 130 to monitor pressure changed within the filtration module. Other instruments may be added by those skilled in the art to monitor various parameters within the filtration module; an air inlet assembly 32 containing a sterilizing air filter and the means for attaching to air inlet port 21. The double arrow 23 illustrates the two directions for air flow to and from pump chamber 8, resulting in pump action.

Figure 14:
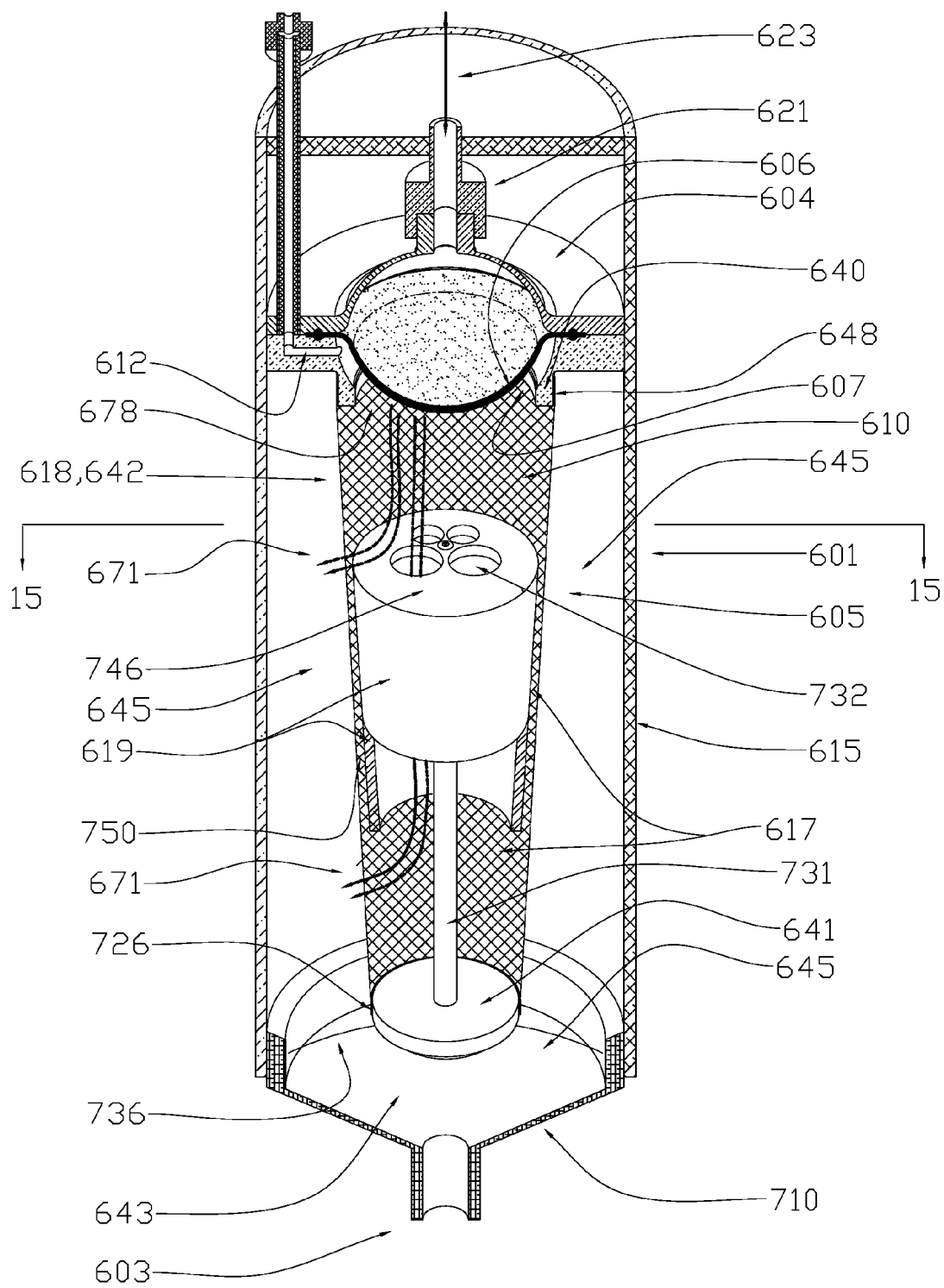
FIG. 14. Sectional view of a compartmentalized filtration module of the invention, also showing a non-sectional views a portion of the module, the views being center isometric, the module an example of one where the flow barrier is internal to the retentate chamber.
Figure 15:
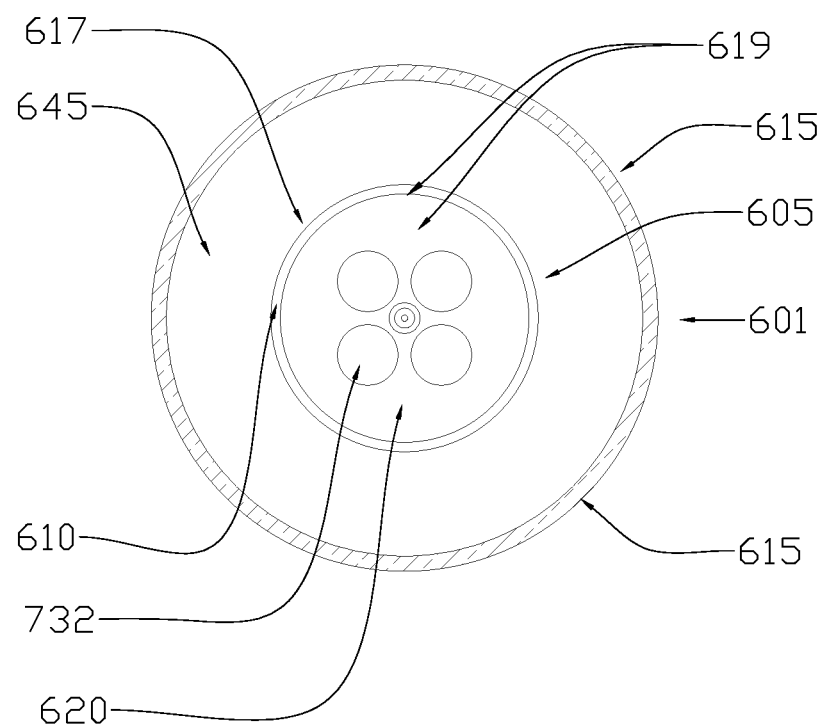
FIG. 15. Sectional view of the compartmentalized filtration module of the invention shown in section in FIG. 14 wherein the sectional view is along the line 15-15 in FIG. 14, but for the entire module, not just the portion of the module shown in cross section in FIG. 14.

FIGS. 14 and 15 together demonstrate another variation of the screen filter module 605 and the compartmentalized filtration module 601. The variations are the second and fourth aspects of the invention (used for the sixth aspect), respectively. While variation in FIG. 14 shows a sectional view of a compartmentalized filtration module of the invention, it also shows non-sectional views of a portion of the module, the views being center isometric. In these variations, the module is an example of one where the flow barrier 619 is internal to the filtrate chamber 610. FIG. 15 is a sectional view of the compartmentalized filtration module of the invention shown in section in FIG. 14. (In FIG. 15, the circular ring for the filter screen 617 is represented by a solid line but in fact represents a cross section of the filter screen 617). The filtrate chamber 610 is inside the screen 617 and the retentate chamber 645 is external to the screen; noting also that the barrier 619 is within the inner perimeter of the screen 617 and unlike the previous examples the screen filter module 605 is inverted and immersed in retentate. notwithstanding those differences, the two versions are similar in most other respects; both, filtrate and retentate chamber share a common screen wall 660; pump 604 which pumps filtrate reversibly into the filtrate chamber 610 which flows reversibly across the screen 617 into the retentate chamber, which retentate flows reversibly between said chamber and culture vessel through connecting conduit 603; noting other similar features: barrier 619, now located within the screen 617 and within the screen filter module 605, has a similar functions to previously ascribed to the external barrier; their function remains largely to direct fluid flow across the screen 617; platform 746, which again directs filtrate flow from the filtrate chamber 610 to the retentate chamber 645, preferably, at its more distal end from retentate chamber entrance 643, dislodging microcarriers attached to the retentate screen wall 660 and facilitating their return to the culture vessel as before; further, openings 732 whose size and configuration may used to control the extent of filtrate flow between the distal and proximal segments, (relative to the retentate entrance 643), of the filtrate chamber 610, thereby, controlling the extent of flow across different segments of the screen. Addition of air to pump chamber 608, as previously described, generates flow from the filtrate chamber to the retentate chamber, towards the culture vessel; one such flow direction is shown by lines 671. Exhausting chamber 608 reverses the flow direction as previously described. Means for removal of filtered harvest through the harvest port 612 is shown. The lower adapter 641 is the counterpart of upper adapters 41, 241 or 441 when it is used in FIGS. 1 through 13. Specific to FIGS. 14 and 15 are the upper barrier surface 746, the wires 736 which function as a stabilizing elements for the screen filter module by virtue of their attachment to base adapter 710.

Also shown in FIGS. 14 and/or 15 are fluid connector 603, alternating pump 604, fluid chamber 607, harvest port 612, outer filtrate chamber wall 615, upper area 618 of the screen, screen filter exit end 642, retentate chamber entrance 643, retentate chamber 645, glue adhesive layer 648, flow lines 671, adhesive layer 726, center post 731, and small openings 732 (four are shown) in the barrier 619, and bypass space 750.

FIG. 16 illustrates a filtration module 401 where the pump 404 is not directly attached to the filtration module, but which nevertheless, generates alternating flow as previously described; the alternating flow is transferred from pump into the filtration module through conduit 461, entering the filtration module filtrate chamber 410 through the filtrate chamber entrance 478. The flow dynamics through the filtration module remain otherwise similar to that shown in FIGS. 11a and 11b. The numbering and meaning of parts in FIG. 16 remain essentially the same as those in FIGS. 11a and 11b. The separation of the pump from the module offers some benefits, including simplified scale up capability and the potential for greater pump flow control capability.

What is claimed is:

1. A screen filter module enhanced with an external barrier, the module comprising:
   a) a retentate chamber, said chamber comprising a chamber wall and a chamber entrance, said chamber entrance permitting fluid containing suspended particulate matter to enter or exit the chamber, and wherein the chamber wall comprises a filter screen, said screen comprising pores, such that said screen permits fluid and particles smaller than the pores but not suspended particulate matter larger than the pores to flow through it;
   b) a barrier, said barrier positioned exterior to the retentate chamber so as to redirect fluid moving through the filter screen area proximal to the chamber entrance so that the redirected fluid moves towards a filter screen area more distal to the chamber entrance;
   c) an exiting space between the filter screen and the barrier, said space for permitting fluid flow;
   d) an opening between the filter screen and the perimeter of the barrier, said opening providing a means for fluid to leave the exiting space and escape the module; and
   e) an upper adapter for attachment to the filter screen, said adapter also attached to a rigid portion of the screen filter module, so as to prevent collapse of the filter screen.

2. The screen filter module of claim 1 wherein the filter screen is either tubular or tapered.

3. The screen filter module of claim 1 wherein the filter screen module further comprises a base adapter for attaching the barrier to the retentate chamber.

4. A screen filter module of claim 1 wherein wherein the pore size diameter of the filter screen is in the range 0.1 microns to 80 microns.

5. A screen filter module of claim 1 wherein the area of the filter screen is in the range between 10 and 10.000 $cm^2$.

6. A screen filter module enhanced with an internal barrier, the module comprising:
   a) a filtrate chamber, said chamber comprising a chamber wall and a chamber entrance, said chamber entrance permitting fluid to exit or enter the chamber, and wherein the chamber wall comprises a filter screen, said screen comprising pores, such that said screen permits fluid and particles smaller than the pores but not suspended particulate matter that is larger than the pores, to flow through it;
   b) a barrier, said barrier positioned inside the filtrate chamber so as to redirect filtrate chamber fluid moving towards a filter screen area distal to the filtrate chamber entrance so that the redirected fluid moves within the filtrate chamber towards a filter screen area more proximal to the filtrate chamber entrance and exits the filtrate chamber so as to flow into the retentate chamber;
   c) an opening in said barrier to allow limited fluid flow through the barrier;
   d) a bypass space between said barrier and the filtrate chamber wall, said space for permitting fluid entering the filtrate chamber through the filter screen to bypass the barrier and flow to the filtrate chamber exit; and
   e) a lower adapter attached to the filter screen.

7. A screen filter module of claim 6 wherein wherein the pore size diameter of the filter screen is in the range 0.1 microns to 80 microns.

8. A screen filter module of claim 6 wherein the area of the filter screen is in the range between 10 and 10.000 $cm^2$.

9. A compartmentalized filtration module that contains a screen module enhanced with an external barrier such that the screen filter module comprises a retentate chamber, the filtration module comprising:
   a) a retentate chamber, said retentate chamber comprising a retentate chamber wall and a retentate chamber entrance, said entrance permitting fluid containing suspended particulate matter to enter and exit the chamber, said retentate chamber wall comprising a filter screen, said screen comprising pores, such that said that said screen permits fluid and particles smaller than said pores but not suspended particulate matter larger than the pores to flow through it;
   b) a filtrate chamber adjoining said retentate chamber, said filtrate chamber comprising a filtrate chamber wall and a filtrate chamber entrance, said filtrate chamber wall comprising the filter screen also comprised by the retentate chamber wall, said filtrate chamber entrance permitting fluid to enter or exit the filtrate chamber;
   c) an alternating pump connected to the filtrate chamber entrance, said pump for pumping fluid in alternating directions through the filtrate chamber entrance and thereby for pumping fluid in alternating directions through the filter screen;
   d) a barrier, said barrier positioned inside the filtrate chamber so as to redirect fluid moving through the filter screen area proximal to the retentate chamber entrance so that the redirected fluid moves towards a filter screen area more distal to the retentate chamber entrance;
   e) an exiting space between the filter screen and the barrier, said space for permitting fluid flow;
   f) an opening between the filter screen and the perimeter of the barrier, said opening providing a means for fluid to escape the exiting space and the retentate chamber;
   g) an upper adapter for attachment to the filter screen said adapter also attached to a rigid portion of the screen filter module, so as to prevent collapse of the filter screen; and
   h) a harvest port for removing fluid from the filtrate chamber.

10. The compartmentalized filtration module of claim 9, which module further comprises a base adapter for attaching the barrier to the retentate chamber and anchoring the filter screen module.

11. The compartmentalized filtration module of claim 9 wherein the entrances to the retentate and filtrate chambers and the alternating pump are aligned along the main axis of symmetry of the screen filter module.

12. The compartmentalized filtration module of claim 9 wherein the barrier redirects fluid away from a portion of the filter that extends from the filter entrance to between 50 percent and 99 percent of the entire length of the filter towards where the filter meets the upper adapter.

13. The compartmentalized filtration module of claim 9 wherein the filter screen is pleated.

14. A compartmentalized filtration module of claim 9 wherein wherein the pore size diameter of the filter screen is in the range 0.1 microns to 80 microns.

15. A compartmentalized filtration module of claim 9 wherein the area of the filter screen is in the range between 10 and 10.000 $cm^2$.

16. A compartmentalized filtration module that contains a screen filter module enhanced with an internal barrier such that the screen filter module functions as the filtrate chamber, the filtration module comprising:
   a) a retentate chamber, said retentate chamber comprising a retentate chamber wall and a retentate chamber entrance, said entrance permitting fluid containing suspended particulate matter to enter and exit the chamber, said retentate chamber wall comprising a filter screen, said screen comprising pores such that said screen permits fluid and particles smaller than said pores but not suspended particulate matter larger than said pores to flow through it;
b) a filtrate chamber adjoining said retentate chamber, said filtrate chamber comprising a filtrate chamber wall and a filtrate chamber entrance, said filtrate chamber wall comprising the filter screen also comprised by the retentate chamber wall, said filtrate chamber entrance permitting fluid to enter or exit the filtrate chamber;
c) an alternating pump connected to the filtrate chamber entrance, said pump for pumping fluid in alternating directions through the filtrate chamber entrance and thereby for pumping fluid in alternating directions through the filter screen;
d) a barrier, said barrier positioned inside the filtrate chamber for redirecting fluid moving towards a filter screen area distal to the filtrate chamber entrance so that said redirected fluid moves through the filter screen area more proximal to the filtrate chamber entrance;
e) a bypass space between said barrier and the filtrate chamber wall, said space for permitting fluid entering the filtrate chamber through the filter screen to bypass the barrier and flow to the filtrate chamber entrance;
f) an opening in said barrier to allow limited fluid flow through the barrier;
g) a lower adapter for attachment to the filter screen, said adapter also attached to a rigid portion of the filtration module, so as to prevent movement of the filter screen; and
h) a harvest port connected to said alternating pump, said port for removing fluid pumped from the filtrate chamber.

17. The compartmentalized filtration module of claim 16, which module further comprises a base adapter for attaching the barrier to the filtrate chamber and anchoring the filter screen module.

18. The compartmentalized filtration module of claim 16 wherein the entrances to the retentate and filtrate chambers and the alternating pump are aligned along the main axis of symmetry of the screen filter module.

19. A compartmentalized filtration module of claim 16 wherein the pore size diameter of the filter screen is in the range 0.1 microns to 80 microns.

20. A compartmentalized filtration module of claim 16 wherein the area of the filter screen is in the range between 10 and 10.000 cm$^2$.

21. A process for removing particulate matter from a fluid in which it is suspended, the process being an example of one that utilizes the screen filter module enhanced with an external barrier, the process comprising the steps of:
a) feeding a suspension into a retentate chamber via an entrance in that chamber, said entrance being the retentate chamber entrance, said suspension comprising the particulate matter suspended in the fluid, said retentate chamber connected to a filtrate chamber via a shared filter screen in their respective walls, said filter screen comprising pores of a size that allow the fluid and particles smaller than the screen pores but not the suspended particulate matter that are larger than the screen pores to pass through, said filtrate chamber comprising an entrance connected to an alternating pump;
b) directing the suspension at the filter screen so that fluid but not said suspended particulate matter passes through the filter screen, said directing achieved by the action of the alternating pump;
c) collecting, in the filtrate chamber, the fluid that passed through the screen filter, said collected fluid being the filtrate fluid;
d) removing a portion of the filtrate fluid from the filtrate chamber, thereby leaving unremoved filtrate fluid in the filtrate chamber;
e) directing the unremoved filtrate fluid back at the screen filter, such filter screen directing achieved by the alternating pump exerting a force on said unremoved filtrate fluid, such that a barrier redirects filtrate fluid moving towards a filter screen area proximal to the retentate chamber entrance so that the redirected fluid moves towards a screen filter area more distal to the retentate chamber entrance; and
f) repeating steps (a) through (e).

22. A process for removing particulate matter from a fluid in which it is suspended, the process being an example of one that utilizes the screen filter module enhanced with an internal barrier, the process comprising the steps of:
a) feeding a suspension into a retentate chamber via an entrance in that chamber, said entrance being the retentate chamber entrance, said suspension comprising the particulate matter suspended in the fluid, said retentate chamber connected to a filtrate chamber via a shared filter screen in their respective walls, said filter screen comprising pores, said pores of a size that allow the fluid and particles smaller than the pores but not the suspended particulate matter that are larger than the screen pores to pass through, said filtrate chamber comprising an entrance connected to an alternating pump;
b) directing the suspension at the screen so that fluid but not said suspended particulate matter passes through the filter screen, said directing achieved by the action of the alternating pump;
c) collecting, in the filtrate chamber, the fluid that passed through the filter screen, said collected fluid being the filtrate fluid;
d) removing a portion of the filtrate fluid from the filtrate chamber, thereby leaving unremoved filtrate fluid in the filtrate chamber;
e) directing the unremoved filtrate fluid back at the screen filter, such directing achieved by the alternating pump exerting a force on said unremoved filtrate fluid, such that a barrier redirects fluid moving towards a screen filter area distal to the filtrate chamber entrance so that the redirected fluid moves towards a screen filter area more proximal to the filtrate chamber exit; and
f) Repeating steps (a) through (e).

* * * * *

UNITED STATES PATENT AND TRADEMARK OFFICE
CERTIFICATE OF CORRECTION

PATENT NO.         : 9,050,547 B2                                   Page 1 of 1
APPLICATION NO.    : 12/565605
DATED              : June 9, 2015
INVENTOR(S)        : Jerry Shevitz It is certified that error appears in the above-identified patent and that said Letters Patent is hereby corrected as shown below:

In the claims

In column 15, line 30, in Claim 4, delete "wherein wherein" and insert -- wherein --;

In column 15, line 59, in Claim 7, delete "wherein wherein" and insert -- wherein --;

In column 16, line 6 (approx.), in Claim 9, delete "that said that said" and insert -- that said --;

In column 16, line 53, in Claim 14, delete "wherein wherein" and insert -- wherein --.

Signed and Sealed this
Fifteenth Day of December, 2015

Michelle K. Lee
*Director of the United States Patent and Trademark Office*